United States Patent
Vukicevic et al.

(10) Patent No.: US 12,263,273 B2
(45) Date of Patent: Apr. 1, 2025

(54) POROUS BIOMATERIALS FOR TISSUE REGENERATION

(71) Applicant: MERZ PHARMA GMBH & CO. KGAA, Frankfurt am Main (DE)

(72) Inventors: Radovan Vukicevic, Frankfurt (DE); Alexander Linko, Frankfurt am Main (DE)

(73) Assignee: MERZ PHARMA GMBH &CO. KGAA, Frankfurt am Main (DE)

(*) Notice: Subject to any disclaimer, the term of this patent is extended or adjusted under 35 U.S.C. 154(b) by 27 days.

(21) Appl. No.: 16/975,418

(22) PCT Filed: Mar. 8, 2019

(86) PCT No.: PCT/EP2019/055801
§ 371 (c)(1),
(2) Date: Aug. 25, 2020

(87) PCT Pub. No.: WO2019/175036
PCT Pub. Date: Sep. 19, 2019

(65) Prior Publication Data
US 2021/0008249 A1    Jan. 14, 2021

(30) Foreign Application Priority Data

Mar. 12, 2018 (EP) ..................... 18161300

(51) Int. Cl.
*A61L 27/26* (2006.01)
*A61K 8/02* (2006.01)
(Continued)

(52) U.S. Cl.
CPC ............ *A61L 27/26* (2013.01); *A61K 8/0279* (2013.01); *A61K 8/64* (2013.01); *A61K 8/735* (2013.01);
(Continued)

(58) Field of Classification Search
CPC ........ A61K 8/64; A61K 8/0279; A61K 8/735; A61K 8/736; A61K 2800/84;
(Continued)

(56) References Cited

U.S. PATENT DOCUMENTS

| 5,324,519 A * | 6/1994 | Dunn ...................... A61L 27/58 424/426 |
| 6,987,181 B2 | 1/2006 | Jaschinski et al. |

(Continued)

FOREIGN PATENT DOCUMENTS

| CN | 106237386 | * | 8/2016 |
| EP | 2510017 B1 | | 1/2015 |

(Continued)

OTHER PUBLICATIONS

Shang et al., Intermolecular interactions between natural polysaccharides and silk fibroin protein, Dec. 27, 2012, Carbohydrate Polymers, vol. 93, pp. 561-573. (Year: 2012).*

(Continued)

*Primary Examiner* — Hong Yu
(74) *Attorney, Agent, or Firm* — RAPHAEL BELLUM PLLC

(57) ABSTRACT

The present invention relates to a porous material having a scaffold comprising: one or more fibroin moieties A and one or more polysaccharide moieties B, wherein A and B are directly conjugated with another without an interconnecting linker structure. Moreover, the present invention refers to a method for preparing a porous material. The present invention further relates to an injectable composition comprising a particulate porous material according to the invention and to cosmetic and therapeutic uses thereof such as facial and body re-shaping as well as regenerating tissue.

19 Claims, 5 Drawing Sheets

(51) Int. Cl.
*A61K 8/64* (2006.01)
*A61K 8/73* (2006.01)
*A61L 27/20* (2006.01)
*A61L 27/22* (2006.01)
*A61L 27/56* (2006.01)
*A61Q 19/08* (2006.01)
*C08B 37/08* (2006.01)
*C08L 1/02* (2006.01)
*C08L 5/08* (2006.01)
*C08L 5/10* (2006.01)

(52) U.S. Cl.
CPC .............. *A61K 8/736* (2013.01); *A61L 27/20* (2013.01); *A61L 27/225* (2013.01); *A61L 27/227* (2013.01); *A61L 27/56* (2013.01); *A61Q 19/08* (2013.01); *C08B 37/0072* (2013.01); *C08L 1/02* (2013.01); *C08L 5/08* (2013.01); *C08L 5/10* (2013.01); *A61K 2800/84* (2013.01); *A61K 2800/91* (2013.01); *A61L 2400/06* (2013.01); *A61L 2430/34* (2013.01)

(58) Field of Classification Search
CPC ..... A61K 2800/91; A61L 27/20; A61L 27/26; A61L 27/56; A61L 27/225; A61L 27/227; A61L 2400/06; A61L 2430/34; A61Q 19/08; C08L 1/02; C08L 5/08; C08L 5/10; C08B 37/0072
See application file for complete search history.

(56) References Cited

U.S. PATENT DOCUMENTS

| | | |
|---|---|---|
| 2011/0189292 A1 | 8/2011 | Lebreton et al. |
| 2014/0094410 A1 | 4/2014 | Kaplan et al. |
| 2014/0315828 A1 | 10/2014 | Pavlovic et al. |
| 2016/0095695 A1 | 4/2016 | Altman et al. |
| 2017/0007738 A1 | 1/2017 | Leisk et al. |
| 2018/0055971 A1 | 3/2018 | Yu et al. |

FOREIGN PATENT DOCUMENTS

| | | | |
|---|---|---|---|
| EP | 2510016 B1 | | 8/2016 |
| JP | 1995267822 | * | 10/1995 |
| WO | 2013/071107 A1 | | 5/2013 |
| WO | 2015/149941 A1 | | 10/2015 |
| WO | 2017/162676 A1 | | 9/2017 |

OTHER PUBLICATIONS

He et al., Tissue engineering scaffolds electrospun from cotton cellulose, Sep. 19, 2014, Carbohydrate Polymers, vol. 115, pp. 485-493. (Year: 2015).*

Zhou et al., Enhancement Biocompatibility of Bacterial Cellulose Membrane via Laccase/TEMPO Mediated Grafting of Silk Fibroins, 2017, Fibers and Polymers, vol. 18 No. 8, pp. 1478-1485. (Year: 2017).*

Yu et al. Production of Hollow Bacterial Cellulose Microspheres Using Microfluidics to Form an Injectable Porous Scaffold for Wound Healing, 2016, Advanced Healthcare Materials, vol. 5, pp. 2983-2992. (Year: 2016).*

Cao and Wang (Int. J. Mol. Sci., 2009, 10:1514-1524).
Cheng et al. (Plast. Aesthet. Res., 2016, 3:92-99).
Kovacina et al. (ACS Biomater. Sci. Eng., 2015, 1:260-270).
Kundu et al. (Advanced Drug Delivery Review, 2013, 65:457-470).
Prasetyo et al. (Clinical, Cosmetic and Investigational Dermatology, 2016, 9:257-280).
Freddi et al., Journal of Biotechnology, 2006, 125:281-294.
Shang et al., Carbohydrate Polymers, 2013, 93:561-573.
Lin et al., Fibers and Polymers, 2008, 9(2):113-120.

* cited by examiner

POROUS BIOMATERIALS FOR TISSUE REGENERATION

The present invention relates to a porous material that can be used for tissue regeneration. The material has a form of scaffold comprising: one or more fibroin moieties A and one or more polysaccharide moieties B, wherein A and B are directly conjugated with another without an interconnecting linker structure. Moreover, the present invention refers to a method for preparing a porous material. The present invention further proposes an injectable composition comprising a particulate porous material according to the invention, and the cosmetic and therapeutic uses thereof, such as for facial and body re-shaping as well as regenerating tissue.

In the last years, facial and body re-shaping has gained increasing interest. For example, breast reconstruction or augmentation, filling of wrinkles, rejuvenation of the skin, soft-tissue augmentation of other kind, etc., are frequently performed. In order to avoid the need of surgical interventions in this context, a number of dermal fillers that can be injected subcutaneously or within the deeper layers of the skin have been developed or are under development. An update of recent skin fillers is provided in Cheng et al. (Plast. Aesthet. Res., 2016, 3:92-99). Herein, also hyaluronic acids are described as potential skin fillers. Likewise, Prasetyo et al. (Clinical, Cosmetic and Investigational Dermatology, 2016, 9:257-280) teach soft-tissue augmentation and rejuvenation by means of hyaluronic acid fillers.

Hyaluronic acid has a good biological acceptability. However, one major drawback is that biodegradation of such material based on hyaluronic acid is comparably rapid and the filler material is not suitable for long term solutions. Thus, there is the need for provision of further filling materials that have improved biological stability. On the other hand, fibroin-based materials are well known for decades. These often have a rather higher biological stability, see Cao and Wang (Int. J. Mol. Sci., 2009, 10:1514-1524).

WO 2013/071107 describes injectable silk fibroin particles that can optionally be loaded with one or more active agents. Kundu et al. (Advanced Drug Delivery Review, 2013, 65:457-470) describes further silk fibroin biomaterials obtainable from freeze-thaw cycles. US-A 2014/094410 describes a porous structure comprising silk fibroin and processes for preparing such, wherein a variety of other ingredients can be added to the porous structure as unbound components.

Kovacina et al. (ACS Biomater. Sci. Eng., 2015, 1:260-270) describes lyophilized silk sponges. US-A 2016/095695 describes hydrogels made of silk fibroin and the use in combination with other means for breast reconstruction or augmentation. However, the structure of such fibroin-based materials is typically rather rigid and compact and shows limited water uptake. Therefore, the aforementioned fibroin-based structures have a number of disadvantages such as rather poor water uptake capability.

Attempts were made to improve the material properties by simple mixing silk fibroin with unbound hyaluronic acid. US-A 2011/0189292 describes such unbound mixtures. The obtained materials do, however, not show stability to a degree that is desired for a number of cosmetic and therapeutic uses. Therefore, attempts have been made to improve the material properties further by crosslinking silk fibroin with hyaluronic acid by means of synthetic crosslinkers. US-A 2014/315828 describes a process for crosslinking unmodified hyaluronic acid and fibroin via a multiepoxide or multiamine crosslinking agent. US-A 2014/315828 focuses on the preparation of gels comprising small-sized particles. The obtained dimensionally stable hydrogels comprise undesirable crosslinking agents that are typically of non-natural origin. This does however not result in a desirable porous material. Furthermore, residues originating from such crosslinking agents used in US-A 2014/315828 are typically incorporated in the obtained material as undesired interconnecting linker structures.

The materials known in the art have an insufficient capability of regeneration of tissue by the body's own cells due to their either poor stability in aqueous buffers as hyaluronic acid or poor porosity like the fibroin-based materials known in the art. Further, many materials disclosed in the prior art contain undesired interconnecting linker structures.

In view of above, there is still an unmet need for porous materials that overcome these drawbacks and, concomitantly, are free of synthetic crosslinking agents or moieties thereof. Preferably, these porous materials should be injectable for cosmetic augmentation, face and body re-shaping and/or for tissue regeneration.

Surprisingly, it has been found that a porous material having (in a form of) a scaffold, comprising fibroin moieties and polysaccharide moieties covalently conjugated with another has the aforementioned particularly beneficial properties. This porous material is well biocompatible, highly and stably porous, has a highly hydrophilic surface and has a restricted swelling over time. It may be well used as a dermal filler.

Accordingly, a first aspect of the present invention relates to a porous material having a (form of a) scaffold comprising:
  one or more fibroin moieties A; and
  one or more polysaccharide moieties B,
wherein A and B are directly conjugated with another without an interconnecting linker structure.

It has been found that such porous material bears unexpectedly beneficial properties. It can take up large amounts of water or aqueous buffers and still remains stable. Preferably, the porous material of the present invention can absorb the 10 to 100-fold, in particular the 20 fold to 50-fold, mass of water or aqueous buffer, related to the dry weight of porous material.

Preferably, the porous material of the present invention is also slowly biodegradable. Alternatively or additionally, the porous material of the present invention may also be used to mimic an extracellular matrix and may, thus, induce cell proliferation. It may be well used as a dermal filler which may be populated by cells.

As used in the context of the present invention, the term "porous material" may be understood the broadest sense as any material that bears pores, in other word having a sponge-like structure. The pores may be interconnected, partly interconnected or separated from another. Often, there will be a mixture of interconnected, partly interconnected or separated pores. Preferably, in an uncompressed form, the sum of the overall inner pore volume (typically filed with air in dry state and with a liquid or viscous fluid in wet state) of a porous material is larger than the overall volume of the solid content of said porous material. In other words, the macroscopic volume of the porous material is preferably mainly composed of pore volume.

As used in the context of the present invention, the term "fibroin moiety" may be understood in the broadest sense as any moiety of fibroin known in the art. Preferably, the fibroin moiety A is a polymeric moiety or a complex of polymeric moieties of a total molecular weight (Mw) of at least 5 kDa (5000 Dalton, 5 Kilodalton), more preferably at least at least 10 kDa (10000 Dalton), even more preferably at least 100 kDa, in particular at least 200 kDa or more. As used throughout the present invention, the molecular weight (Mw) is preferably the weight average molecular weight of the characterized species. The fibroin moiety A may have one or more backbones (amide/protein backbones) of one or more full-length fibroin polypeptides and/or one or more fibroin polypeptides or a complex of two or more thereof. Preferably, the fibroin moiety A comprises at least one backbone of a full-length fibroin polypeptide, in particular (essentially) consists of one or more backbones of one or more full-length fibroin polypeptides. In other words, the fibroin moiety A is preferably derived from naturally occurring fibroin.

The term "moiety" in the context of the fibroin moiety A means that the one or more fibroin backbones may bind to one or more other structures such as, in particular, the one or more polysaccharide moieties B. It will be understood that the term "fibroin moiety" may also include salts and modified forms thereof. Preferably, the fibroin moiety A comprises one or more lysyl residues that may optionally be bound to the polysaccharide moiety B.

As used in the context of the present invention, the term "fibroin" may be understood the broadest sense as any fibroin known in the art. Fibroin may be obtained from a commercial supplier (e.g., Advanced BioMatrix, USA (e.g. product No. 5154-20ML); CareSilk, Italy (e.g. product No. CSK10-1051)) or may be prepared from a natural source or by means of genetic or rather synthetic engineering.

In a preferred embodiment, fibroin is silk fibroin. In an alternative preferred embodiment, fibroin is a polypeptide or a complex of two or more polypeptides having at least 80%, more preferably at least 90%, even more preferably at least 95%, even more preferably at least 98% sequence homology, in particular identity, to one or more naturally occurring silk fibroin polypeptides. Silk fibroin may also include a truncated form thereof. Silk fibroin may be silkworm (*Bombyx mori*) fibroin and insect or spider silk fibroin.

For example, it may be fibroin of *Bombyx mori* or, alternatively, a species selected from the group consisting of *Antheraea, Cricula, Sami, Gonometa* an *Nephila* (e.g., *Nephila clavipes*) species or a homologue of having at least 80%, more preferably at least 90%, even more preferably at least 95%, even more preferably at least 98% sequence homology, in particular identity, to one of the aforementioned or a truncated form thereof. It will be understood that also mixtures of different fibroins may be used.

In a highly preferred embodiment, fibroin is ((essentially) complete) silkworm (*Bombyx mori*) fibroin. In a particularly preferred embodiment, fibroin is silkworm fibroin obtainable or obtained from *Bombyx mori*.

Silkworm fibroin may be obtained from silkworm cocoons. The process of obtaining silk from silkworm is well-known in the art. For example, silkworm cocoons may be boiled for about 30 min (minutes) in an aqueous solution. Optionally, the aqueous solution may comprise about 0.02 M $Na_2CO_3$. The cocoons may be rinsed with water or an aqueous buffer to extract the sericin proteins and the extracted fibroin may be dissolved in an aqueous buffer. Salts that may be used for this purpose may, exemplarily, include lithium bromide, lithium thiocyanate, calcium nitrate and mixtures thereof. Optionally, the extracted fibroin may be dissolved in about 9-12 M lithium bromide solution. The salt may be removed by any means, e.g., dialysis. In a preferred embodiment, other components of the silkworm cocoons have been (essentially) removed such as, e.g., sericin. Thus, preferably, at least 50 wt. %, in more preferably at least 75 wt. %, even more preferably at least 80 wt. %, particular at least 90 wt. %, of the sericin initially contained in the silkworm cocoon have been removed. Silk fibroin may be type I, type II or type III silk fibroin or a mixture of two or more thereof. Preferably, fibroin is or comprises type I silk fibroin.

Alternatively, one or more fibroin polypeptides, including silkworm fibroin polypeptides and complete silkworm fibroin, may also be obtained by means of genetic engineering. Genetically engineered fibroin may be, for example, obtained from bacteria, insect cells, spider cells, yeast, mammalian cells, transgenic animals, or transgenic plants.

Optionally, fibroin may be modified by any means such as, e.g., covalent bonding, or modifications through charge-charge interaction. Exemplary chemical modification methods include, but are not limited to, carbodiimide coupling reaction, diazonium coupling reaction, avidin-biotin interaction and pegylation with a chemically active or activated derivatives of the PEG polymer. Fibroin can also be modified through gene modification to alter functionalities of the protein.

Fibroin may bear the properties as described in the art such as described in any of WO 2013/071107, US-A 2014/094410, US-A 2016/095695, US-A 2011/189292, US-A 2014/315828), Cao and Wang (Int. J. Mol. Sci., 2009, 10:1514-1524), Kundu et al. (Advanced Drug Delivery Review, 2013, 65:457-470) and Kovacina et al. (ACS Biomater. Sci. Eng., 2015, 1:260-270).

According to the present invention, the one or more fibroin moieties A may be conjugated with the one or more polysaccharide moieties B by any means and via any functional groups thereof. According to the present invention, the one or more fibroin moieties A and the one or more polysaccharide moieties B directly conjugated with another without an interconnecting linker structure (i.e., preferably without a synthetic crosslinker). Preferably, one or more of the functional groups of the one or more fibroin moieties A may bind to one or more of the functional groups of the one or more polysaccharide moieties B. Preferably, the one or more fibroin moieties A and the one or more polysaccharide moieties B covalently conjugated with another without an interconnecting linker structure.

Preferably, one or more of the functional groups of the one or more fibroin moieties A may covalently bind to one or more of the functional groups of the one or more polysaccharide moieties. In other words, preferably, A and B are directly covalently bond with another. Such covalent bond may be any covalent bond that can be formed between A and B. The chemical structure of the covalent bound may depend on the functional groups thereof, it may, for example, without any limitation, be selected from the group consisting of —NH—CO—, =N—, —O—CO—, —NH—CO—NH—, —NH—CO—O—, —O—, —NH—, —NR—, and tautomers thereof, each in both directions, wherein R is an organic residue. In this context, an organic residue may be any organic residue, preferably a residue of one or more fibroin moieties A, one or more polysaccharide moieties B or a conjugate of two or more thereof, or an organic residue of 1 to 20 carbon atoms (e.g., —$CH_3$, —$CH_2CH_3$, —$CH_2F$, —$CHF_2$, or —$CF_3$).

In a preferred embodiment, one or more lysyl residues of the one or more fibroin moieties A are directly covalently bound to one or more carbon atoms of the one or more polysaccharide moieties B via double bond or via single bond.

Preferably, one or more lysyl residues of the one or more fibroin moieties A are directly covalently bound to one or more carbon atoms of the one or more polysaccharide moieties B via a bond selected from the group consisting of =N—, —NH—, —NR—, —NH—CO— and tautomers thereof, wherein the nitrogen atom (N) is preferably the nitrogen atom of a fibroin moiety A, in particular of the epsilon amino group of a lysyl residue of a fibroin moiety A.

As used in the context of the present invention, the term "polysaccharide moiety" may be understood the broadest sense as any moiety of a polysaccharide known in the art. Preferably, the polysaccharide comprises hydroxy groups. Preferably, the polysaccharide moiety B is a polymeric moiety of a molecular weight (Mw) of at least 1 kDa (1000 Da), more preferably at least 5 kDa, even more preferably at least 10 kDa, even more preferably at least 50 kDa, even more preferably at least 100 kDa, even more preferably at least 200 kDa, even more preferably at least 300 kDa or more. Preferably, the one or more polysaccharide moieties B have a weight average molecular weight (Mw) in the range of from 10 to 10000 kDa.

In a more preferred embodiment, the one or more polysaccharide moieties B have a weight average molecular weight (Mw) in the range of from 50 to 2000 kDa.

More preferably, the one or more polysaccharide moieties B have a weight average Mw in the range of from 100 to 10000 kDa. Even more preferably, it may have a molecular weight in the range of from 100 and 5000 kDa, of from 200 to 2000 kDa, of from 250 to 1500 kDa, of from 300 to 1000 kDa, of from 400 to 900 kDa or of from 500 to 900 kDa.

The term "moiety" in the context of the polysaccharide moiety B means that the polysaccharide backbone is bond to one or more other structures such as, in particular, the one or more fibroin moieties A. It will be understood that the term "polysaccharide moiety" may also include salts and modified forms thereof, in particular when the backbone of fibroin or a truncated form thereof is (essentially) maintained. Typically, the polysaccharide has been partly oxidized. This is described in more detail herein.

As used in the context of the present invention, the term "polysaccharide" may be understood the broadest sense as any polysaccharide in the art. It may a naturally occurring polysaccharide that may be modified or may be a synthetic polysaccharide. The polysaccharide may be branched or unbranched.

In a preferred embodiment, the one or more polysaccharide moieties B are selected from the group consisting of hyaluronic acid moieties, cellulose moieties, heparosan moieties and mixtures of two or more thereof.

Hyaluronic acid (HA) may be understood in the broadest sense as any hyaluronic acid in the art. In a preferred embodiment, hyaluronic acid (HA) is a naturally glycosaminoglycan composed of linked repeating units of V-acetyl-D-glucosamine and D-glucuronic acid ([alpha-1,4-D-glucuronic acid-beta-1,3-N-acetyl-D-glucosamine]$_n$). Accordingly, the repeating unit of hyaluronic acid (HA) may be the following:

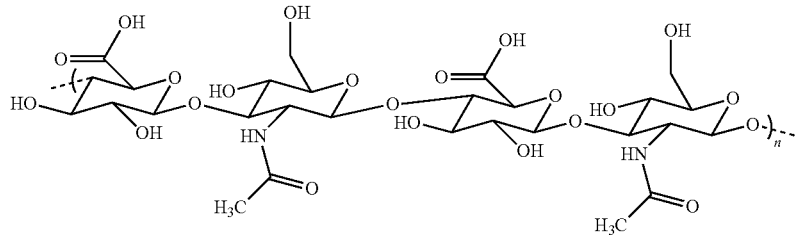

Hyaluronic acid (HA) may be defined as in WO 2017/162676. The molecular weight (Mw) of hyaluronic acid (HA) in the context of the present invention is preferably in the range of from 10 to 10000 kDa. In a more preferred embodiment, hyaluronic acid has a weight average molecular weight (Mw) in the range of from 50 to 2000 kDa. More preferably, hyaluronic acid has a weight average Mw in the range of from 100 to 10000 kDa. Even more preferably, it may have a molecular weight in the range of from 100 to 5000 kDa, of from 200 to 2000 kDa, of from 250 to 1500 kDa, of from 300 to 1000 kDa, of from 400 to 900 kDa or of from 500 to 900 kDa.

Heparosan may be understood in the broadest sense as any heparosan. In a preferred embodiment, it may be such as described in WO 2015/149941. Heparosan (HEP) is a biopolymer belonging to the glycosaminoglycan (GAG) family of polysaccharides.

In humans, it is an intermediate product in the biosynthesis of heparin and heparin sulfate. The structure of heparosan is highly similar to that of hyaluronic acid (HA) since it has the same monosaccharide component sugars as hyaluronic acid and differs from HA only in that the beta-(1,3) glycosidic bond between the glucuronic acid (GlcUA) and the N-acetylglucosamine (GlcNAc) in HA is replaced by a beta-(1,4) glycosidic bond in HEP and in that the beta-(1,4) glycosidic bond between N-acetylglucosamine (GlcNAc)

and the glucuronic acid (GlcUA) in HA is replaced by an alpha-(1,4) glycosidic bond in HEP:

GlcUA-beta-(1-4)-[GlcNAc-alpha-(1-4)-GlcUA-beta-(1-4)]$_n$-GlcNAc HEP

Typically, heparosan has excellent biocompatibility. Heparosan carries a high number of negative charges and hydroxyl groups and is therefore highly hydrophilic, which increases tissue compatibility. Furthermore, due to the fact that heparosan polymers, even after modification, still comprise stretches that occur in natural heparan sulfate and heparin polymers, heparosan is typically non-immunogenic (e.g., does not induce antibodies). Moreover, due to the structural similarity between heparosan and hyaluronic acid, the same chemical modifications, including oxidation to aldehydes as that known for hyaluronic acid may be made on the functional groups. The molecular weight (Mw) of the heparosan polymers used in the context of the present invention may range from about 5 kDa to about 7000 kDa, preferably from about 10 kDa to about 5000 kDa, even more preferably from about 10 kDa to about 3500 kDa, even more preferably from about 20 kDa to about 1000 kDa, even more preferably from about 50 kDa to about 800 kDa, in particular from about 30 kDa to about 700 kDa.

Cellulose may be understood in the broadest sense as any cellulose. In a preferred embodiment, it may be such as described in U.S. Pat. No. 6,987,181. Cellulose may further preferably bear the characteristics as described for the polysaccharide herein. Cellulose may be obtained commercially. It may be partly oxidized as described in U.S. Pat. No. 6,987,181 and laid out in the context of the method below. Preferably, cellulose as used herein is (essentially) purified from lignin.

In a preferred embodiment of the present invention, the one or more polysaccharide moieties B may be bound to the one or more fibroin moieties A via reaction of one or more aldehyde groups, more preferably of one or more aldehyde groups of the one or more polysaccharide moieties B, in particular of one or more aldehyde groups of the one or more polysaccharide moieties B with the epsilon amino group of a lysyl residue of the one or more fibroin moieties A.

Accordingly, in a preferred embodiment, the polysaccharide moiety B that, before reacting with the one or more fibroin moieties A, comprised one or more aldehyde groups may be obtained by partly oxidizing the polysaccharide B. Such partly oxidized polysaccharide may also be interchangeably designated as aldehyde modified polysaccharide or formyl polysaccharide (formyl polysaccharide). Such partly oxidized polysaccharide may be obtained by any means. It can also be commercially obtained. Alternatively, the oxidation of hyaluronic acid may also be conducted by mild oxidation agents. This is exemplified more in detail in the context of the method as laid out below and, mutatis mutandis, also applies in the context of the porous materials and the conjugate as described herein.

In a more preferred embodiment, the polysaccharide comprising aldehyde groups may be partly oxidized hyaluronic acid. Such partly oxidized hyaluronic acid may also be interchangeably designated as aldehyde modified hyaluronic acid or formyl hyaluronic acid (formyl HA). Such partly oxidized hyaluronic acid may be obtained by any means. It can also be commercially obtained. Alternatively, the oxidation of hyaluronic acid may also be conducted by mild oxidation agents.

A highly preferred embodiment of the present invention relates to a porous material having a scaffold comprising:
    one or more silk fibroin moieties A; and
    one or more hyaluronic acid moieties B,
wherein A and B are directly covalently conjugated with another without an interconnecting linker structure.

The ratio between fibroin moieties A and polysaccharide moieties B may be any ratio, preferably in the (mass) ratio A:B in the range of from 1:100 to 100:1. In a preferred embodiment, the (mass) ratio between fibroin moieties A and polysaccharide moieties B is in the range of from 1:10 to 10:1. As used throughout the present invention, the ratio A:B is the mass ratio. More preferably, the (mass) ratio between fibroin moieties A and polysaccharide moieties B (A:B) is in the range of from 1:8 to 8:1, even more preferably in the range of from 1:3 to 6:1, even more preferably in the range of from 1:2 to 5:1, in particular in the range of from 1:1 to 1:3.

When particularly high water/buffer absorbance is desired, the polysaccharide moieties B may be used in mass excess. When particularly high stability is desired, the fibroin moieties A may be used in larger mass excess.

A highly preferred embodiment of the present invention relates to a porous material having a scaffold comprising:
    one or more silk fibroin moieties A; and
    one or more hyaluronic acid moieties B,
wherein the (mass) ratio between A and B is in the range of from 1:10 to 10:1, and wherein A and B are directly covalently conjugated with another without an interconnecting linker structure.

The pore size may be any pore size. It may be adjusted by means of adapting the crosslinking by means of adjusting the degree of oxidation. In a preferred embodiment, the porous material bears pores of a mean average pore diameter in the range of from 20 to 400 μm. More preferably, the porous material bears pores of a mean average pore diameter in the range of from 30 to 300 μm, in particular of from 50 to 200 μm. The pore size may be such in the dry or in the water-moist state.

A preferred embodiment of the present invention relates to a porous material that bears pores of a mean average pore diameter in the range of from 20 to 400 μm and has a scaffold comprising:
    one or more fibroin moieties A; and
    one or more polysaccharide moieties B,
wherein the (mass) ratio between A and B is in the range of from 1:10 to 10:1, and wherein A and B are directly covalently conjugated with another without an interconnecting linker structure.

A preferred embodiment of the present invention relates to a porous material that bears pores of a mean average pore diameter in the range of from 20 to 400 μm and has a scaffold comprising:
    one or more silk fibroin moieties A; and
    one or more hyaluronic acid moieties B,
wherein the (mass) ratio between A and B is in the range of from 1:10 to 10:1, and wherein A and B are directly covalently conjugated with another without an interconnecting linker structure.

A preferred embodiment of the present invention relates to a porous material that bears pores of a mean average pore diameter in the range of from 20 to 400 μm and has a scaffold comprising:
    one or more silk fibroin moieties A; and
    one or more hyaluronic acid moieties B having a molecular weight of at least 100 kDa,
wherein the (mass) ratio between A and B is in the range of from 1:10 to 10:1, and wherein A and B are directly covalently conjugated with another without an interconnecting linker structure.

The porous material may be prepared as a block or as smaller particles. In a preferred embodiment, the porous material is particulate and bears a mass average particle size that is at least 5fold larger than the mean average pore diameter. More preferably, porous material is particulate and bears a mass average particle size that is at least 10 fold, in particular at least 20 fold, larger than the mean average pore diameter. A particulate porous material has the advantage that it can be administered to an individual via injection (e.g., via a syringe or a drip).

As used herein, an individual (also: a subject) may be any animal, typically a mammal, preferably a domestic mammal or a human. Particularly preferably, an individual is a human. A treated human can also be designated as a patient, independent on his/her health state.

In a preferred embodiment, the porous material is particulate and bears a mass average particle size in the range of from 100 to 2000 μm in the particles' longest dimensions. More preferably, the porous material is particulate and bears a mass average particle size in the range of from 200 to 1500 μm in the particles' longest dimensions.

In a preferred embodiment, the porous material is particulate and bears a mass average particle size that is at least 5 fold larger than the mean average pore diameter, in particular in the range of from 100 to 2000 μm in the particles' longest dimensions. In an even more preferred embodiment, the porous material is particulate and bears a mass average particle size that is at least 10 fold larger than the mean average pore diameter, in particular in the range of from 200 to 1500 μm in the particles' longest dimensions.

A preferred embodiment of the present invention relates to a porous material that bears pores of a mean average pore diameter in the range of from 20 to 400 μm and has a scaffold comprising:

one or more silk fibroin moieties A having a molecular weight of at least 200 kDa; and one or more hyaluronic acid moieties B having a molecular weight of at least 200 kDa, wherein the (mass) ratio between A and B is in the range of from 1:10 to 10:1, and wherein one or more lysyl residues of the one or more fibroin moieties A are directly covalently bound to one or more carbon atoms of the one or more hyaluronic acid moieties B via double bond or via single bond.

The porous material of the present invention may be prepared by any means suitable for this purpose.

A further aspect of the present invention relates to a method for preparing a porous material, comprising the steps of:
 (i) providing the following components:
  (a) fibroin (a),
  (b) at least one polysaccharide (b) comprising aldehyde groups,
  (c) at least one liquid carrier (c), and
  (d) optionally one or more further components (d);
 (ii) mixing (a), (b) and (c), and optionally (d), with another;
 (iii) freezing the composition obtained from step (ii);
 (iv) lyophilizing the frozen composition obtained from step (iii); and
 (v) heating the lyophilized material obtained from step (iv) to a degree suitble for enabling the formation of covalent bonds between (a) and (b) and removal of residual liquid carrier (c).

It will be understood that the definitions and preferred embodiments as laid out in the context of the porous material above mutatis mutandis apply to the method for preparing a porous material. In a preferred embodiment, the porous material is a porous material according to the present invention.

The step (i) of the method of the present invention of providing the components can be performed by any means.

As laid out above, the fibroin (a) (corresponding to the fibroin moiety A above) may be understood the broadest sense as any fibroin known in the art. Fibroin may be obtained from a commercial supplier (e.g., Advanced BioMatrix, USA (e.g. product No. 5154-20ML); CareSilk, Italy (e.g. product No. CSK10-1051)) or may be prepared from a natural source or by means of genetic engineering. Preferably, the fibroin (a) is stored in a freezer or a liquid gas, e.g. in a temperature range of from −15° C. to −200° C. For example, the fibroin (a) may be stored at approximately −80° C. or in liquid nitrogen (i.e., at approximately −196° C.). the fibroin (a) may bestored in dry state as a powder or as a solution in water (e.g., in a concentration in the range of from 10 to 100 mg/ml (e.g., approximately 50 mg/ml). When thawing a previously frozen solid fibroin or fibroin solution, preferably, the fibroin is preferably protected from air.

As laid out above, the polysaccharide (b) (corresponding to the polysaccharide moiety B above) may be understood the broadest sense as any polysaccharide and is preferably selected from the group consisting of hyaluronic acid moieties, cellulose moieties, heparosan moieties and mixtures of two or more thereof, in particular is hyaluronic acid. According to the present invention, the at least one polysaccharide (b) comprises aldehyde groups. These can be obtained by any means. Some polysaccharides may naturally comprise aldehyde groups. Others may be partly oxidized in order to convert some of the hydroxy groups to aldehyde groups.

The (mass) ratio between fibroin (a) and the one or more polysaccharides (b) may be any ratio. In a preferred embodiment, the (mass) ratio between (a) and (b) is in the range of from 1:10 to 10:1. More preferably, the (mass) ratio (a):(b) is in the range of from 1:8 to 8:1, even more preferably in the range of from 1:3 to 6:1, even more preferably in the range of from 1:2 to 5:1, in particular in the range of from 1:1 to 1:3. When particularly high water/buffer absorbance is desired, (b) may be used in mass excess. When particularly high stability is desired, (a) may be used in larger mass excess.

In a preferred embodiment, the at least polysaccharide (b) bears a (molar) ratio between hydroxy groups and aldehyde groups in the range of from 100:1 to 2:1, in particular of from 90:1 to 5:1.

In a more preferred embodiment, the at least polysaccharide (b) comprises a (molar) ratio between hydroxy groups and aldehyde groups in the range of from 85:1 to 6:1, in particular of 80:1 to 10:1.

In the context of the ratio between hydroxy groups and aldehyde groups, the ratio is preferably a molar ratio. Examples for routes of mild oxidation of polysaccharide, in particular hyaluronic acid, in order to obtain polysaccharide comprising aldehyde groups (e.g., formyl HA) is described in EP-A 2510016 and EP-A 2510017.

Oxidation of polysaccharides is a process in which the oxidation degree of the polysaccharide functional groups is changing. In the context of the present invention, the formation of aldehyde groups is desired. The reaction may be performed by using mild oxidizing agents such as, e.g., agents containing atoms in higher oxidation degrees. For selective oxidation of polysaccharides on the primary hydroxyl group (e.g., the $C_6$-atom of hexose moieties such as, e.g., hyaluronic acid), the system of 2,2,6,6-tetramethyl- 1-piperidinyloxyl radical TEMPO/TCC in dimethylformamide (DMF) at the temperature of 0° C. may be used. The structure of TEMPO is also described in EP-A 2510016.

2,2,6,6-tetramethyl-1-piperidinyloxyl radical (TEMPO)- and NaOCl-mediated oxidation of the primary hydroxyl group of hyaluronic acid to a carboxylic acid may also be performed at pH 10.2 and at the temperature of 0° C. as exemplarily shown in Scheme 2 of EP-A 2510017. This route is particularly preferred. Then, the corresponding aldehyde is typically obtained as the main product. Herein, an increase of the concentration of the salt (e.g., NaBr, NaCl, $Na_2SO_4$) in the solution may be used to decrease the oxidation rate. Alternatively, oxidation may also be performed by adding Dess-Martin periodinane (DMP) in dimethyl sulfoxide (DMSO) or in DMF at a temperature of 20° C. as an oxidizing agent. Numerous alternative routes may be used to obtain a polysaccharide comprising aldehyde groups.

An example for a partly oxidation of cellulose is described in U.S. Pat. No. 6,987,181 (see for example column 9, line 59, through column 10, line 3). Partly oxidizing cellulose may be performed in an aqueous system, e.g., by means of 4-Hydroxy-TEMPO or 4-Acetamido-TEMPO in an amount of 0.5 to 10 wt. % (weight percent), based on the dry weight of the fibrous material, in the presence of NaOCl in an amount of 0.1 to 5 wt. %, based on the dry weight of the fibrous material at a pH of 2 to 10 and a temperature of 5 to 60° C. for 0.25 to 3 h, in order to generate aldehyde functions at position C(6) of the cellulose.

As used herein, the (mass) ratio of oxidized hydroxy groups can also be designated as modification degree (MoD). Preferably, the MoD characterizes the percentage of oxidized hydroxy groups. In other words, it is preferably specified which percentage fraction of hydroxy groups is oxidized into aldehyde groups. Accordingly, the preferred (molar) ratio between hydroxy groups and aldehyde groups of 100:1 to 2:1 can also be designated as a MoD in the range of from approximately 1 to 33 mol % (mol percent). The more preferred (molar) ratio between hydroxy groups and aldehyde groups of from 90:1 to 5:1 can also be designated as a MoD in the range of from approximately 1.1 to 17 mol %. In a highly preferred embodiment, the at least polysaccharide (b) has a modification degree (MoD) in the range of from 0.1 to 33 mol %, more preferably an MoD of from 0.2 to 30 mol %, even more preferably an MoD of from 0.5 to 20 mol %, even more preferably an MoD of from 1 to 15 mol %, in particular an MoD of of from 2 to 10 mol %. Exemplarily, the at least polysaccharide (b) has a modification degree (MoD) of (approximately) 2 mol %, (approximately) 3 mol %, (approximately) 4 mol %, (approximately) 5 mol %, (approximately) 6 mol %, (approximately) 7 mol %, (approximately) 8 mol %, (approximately) 9 mol % or (approximately) 10 mol %.

The liquid carrier (c) may be understood the broadest sense as any liquid that is suitable for step (i) of the method according to the present invention. Therefore, the liquid does preferably (essentially) neither react with the fibroin (a) nor with the polysaccharide (b), in particularly does (essentially) not react with the aldehyde groups of the polysaccharide (b). Furthermore, the fibroin (a) and the polysaccharide (b) are preferably at least partly soluble, more preferably well soluble, in the liquid carrier (c). Accordingly, the liquid carrier (c) preferably is a polar liquid that is not too reactive. Preferably, the liquid carrier (c) is removable by means of lyophilization. Preferably, the liquid carrier (c) may be water, an aqueous buffer or a polar organic liquid (e.g., an alcohol (e.g., ethanol, methanol, etc.)). Preferably, the liquid (d) is pharmaceutically acceptable. Particularly preferably, the liquid carrier (c) is (optionally purified) water.

Optional further components (d) may be any components. An optional further component (d) may be a component that supports the process or may a component that is intended to be incorporated in the porous material.

For example, such optional further component (d) may be selected from the group consisting of one or more local anesthetics, one or more cell proliferation factors, one or more dyes, and combinations of two or more thereof.

Suitable local anesthetics for use herein include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. Combinations of two or more of the mentioned anesthetic agents, for example a combination of lidocaine and other "caine"-anesthetic(s) like prilocaine, may also be used herein.

A local anesthetic may make injection into an individual more comfortable. A cell proliferation factor may improve cellular invasion into an administered porous material. A dye may either improve localization of the injection (e.g., a pharmaceutically acceptable fluorescent dye like fluorescein or rhodamine) or may improve invisibility of the otherwise whitish porous material (e.g., by rendering it flesh-colored). A component (d) may be simply admixed and remain unbound or may be bound to any of the other components.

In a highly preferred embodiment, the method for preparing a porous material comprises the steps of:
 (i) providing the following components:
   (a) silk fibroin (a),
   (b) at least one polysaccharide (b) of a molecular weight of at least 100 kDa comprising aldehyde groups in a (molar) ratio between hydroxy groups and aldehyde groups of 100:1 to 2:1, in particular of 90:1 to 5:1,
   (c) at least one liquid carrier (c), in particular water, and
   (d) optionally one or more further components (d);
 (ii) mixing (a), (b) and (c), and optionally (d), with another;
 (iii) freezing the composition obtained from step (ii);
 (iv) lyophilizing the frozen composition obtained from step (iii); and
 (v) heating the lyophilized material obtained from step (iv) to a degree suitable for enabling the formation of covalent bonds between (a) and (b) and removal of residual liquid carrier (c).

The step (ii) of the method of the present invention of mixing the components a), (b) and (c), and optionally (d), may be performed by any means.

Preferably, the fibroin (a) is dissolved in a liquid carrier (c), in particular in (optionally purified) water, thereby forming a fibroin solution. Preferably, the fibroin (a) concentration in this fibroin solution is in the range of from 0.5 to 100 mg/ml, more preferably 1 to 75 mg/ml, even more preferably 5 to 40 mg/ml, more preferably 10 to 40 mg/ml.

Preferably, the polysaccharide (b) is dissolved in a liquid carrier (c), in particular in (optionally purified) water, thereby forming a polysaccharide solution.

Preferably, the polysaccharide (b) concentration in this polysaccharide solution is in the range of from 0.5 to 100 mg/ml, more preferably 1 to 50 mg/ml, even more preferably 5 to 40 mg/ml, more preferably 10 to 30 mg/ml.

Preferably, the total concentration of polymer components (a) and (b) in the composition may be in any range, e.g. in a range of from 1 to 200 mg/ml, in particular in a range of from 1 to 100 mg/ml.

In a preferred embodiment, in step (ii), the total concentration of polymer components (a) and (b) in the composition is in the range of from 1 to 50 mg/ml.

More preferably, the total concentration of polymer components (a) and (b) in the composition is in the range of from 2 to 50 mg/ml, more preferably in the range of from 10 to 50 mg/ml, in particular in the range of from 20 to 40 mg/ml. For example, it may be in the range of from 10 to 20 mg/ml, of from 20 to 30 mg/ml, of from 30 to 40 mg/ml, or of from 40 to 50 mg/ml.

In a preferred embodiment, the method for preparing a porous material comprises the steps of:
(i) providing the following components:
  (a) silk fibroin (a),
  (b) at least one polysaccharide (b) of a molecular weight of at least 100 kDa comprising aldehyde groups in a (molar) ratio between hydroxy groups and aldehyde groups of 100:1 to 2:1, in particular of 90:1 to 5:1,
  (c) at least one liquid carrier (c), in particular water, and
  (d) optionally one or more further components (d);
(ii) mixing (a), (b) and (c), and optionally (d), with another, wherein the total concentration of (a) and (b) in the composition is in the range of from 1 to 50 mg/ml;
(iii) freezing the composition obtained from step (ii);
(iv) lyophilizing the frozen composition obtained from step (iii); and
(v) heating the lyophilized material obtained from step (iv) to a degree suitable for enabling the formation of covalent bonds between (a) and (b) and removal of residual liquid carrier (c).

Preferably, the fibroin (a) and the polysaccharide (b), and optionally the one or more further components (d), are each dissolved in s well mixable with another. More preferably, the fibroin (a) and the polysaccharide (b), and optionally the one or more further components (d), are each dissolved in the same type of liquid carrier (c), in particular in (optionally purified) water.

In one preferred embodiment, the components (a)-(c), and optionally (d), are mixed in a temperature range from 0° C. to 40° C., in particular at 5° C. to 25° C. In a preferred embodiment, mixing is performed at room temperature (i.e., at (approximately 20° C.). In one preferred embodiment, the components (a)-(c), and optionally (d), are mixed homogeneously. Preferably, upon mixing, no or merely low amounts of air are incorporated. Homogenous mixing may be achieved by any means such as e.g. in one or more syringes, one or more closable vials or the like.

The mixed composition obtained from step (ii) may be brought in any form such as, e.g., poured into a cavity molding (e.g., a dish, a molding, etc.) or an optionally closable vial, an optionally closable syringe, etc.

The step (iii) of the method of the present invention of freezing the composition obtained from step (ii) may be performed by any means. Preferably, freezing is performed in a form in which the mixed composition obtained from step (ii) is present. Alternatively, freezing may be performed by spray freezing. Freezing may be performed at a temperature range of from −5° C. to −200° C. Freezing may be performed in a freezer (e.g., −20° C. or −80° C.) or in a liquid gas (e.g., liquid nitrogen at approximately −196° C.).

The step (iv) of the method of the present invention of lyophilizing the frozen composition obtained from step (iii) may be performed by any means and at any temperature. Preferably, lyophilization is performed at room temperature (RT). Preferably, lyophilization is performed until (most of) the liquid carrier (c) is removed.

The step (v) of the method of the present invention of heating the lyophilized material obtained from step (iv) may be performed by any means. As described above, heating is performed to a degree suitable for enabling the formation of covalent bonds between (a) and (b). Further, the residual liquid carrier (c) may also be removed when performing this step.

When covalent bonds have been formed between the fibroin (a) and the at least one polysaccharide (b), these are designated as fibroin moiety A and polysaccharide moiety B.

In a preferred embodiment, step (v) is a step of water vapor annealing. The dry sample may be taken from its form and may be then be contacted with water vapor. Preferably, the porous material is not contacted with liquid water or any other liquid in this step.

In a preferred embodiment, in step (v), the lyophilized material is heated to a temperature in the range of from 35 to 80° C. More preferably, the temperature used in this step (v) is in the range of from 40 to 70° C., even more preferably in the range of from 40 to 60° C., even more preferably in the range of from 45 to 55° C., in particular a temperature of approximately 50° C.

Preferably, in step (v), the lyophilized material is heated for a time range of from 0.5 to 15 h (hours) (e.g., 0.5 to 6 h). In a preferred embodiment, in step (v), the lyophilized material is heated for a time range of from 1 to 10 h. More preferably, the time range used in this step (v) is in the range of from 90 min to 8 h, even more preferably in the range of from 2 to 6 h, even more preferably in the range of from 300 min to 4 h, in particular for a time of approximately 3 h.

In a more preferred embodiment, in step (v), the lyophilized material is heated at a temperature in the range of from 35 to 80° C. for 1 to 10 h. More preferably, the lyophilized material is heated at a temperature in the range of from 40 to 70° C. for 90 min to 8 h, even more preferably in the range of from 40 to 60° C. for 2 to 6 h, even more preferably in the range of from 45 to 55° C. for 300 min to 4 h, in particular in the range of approximately 50° C. for approximately 3 h.

In a highly preferred embodiment, the method for preparing a porous material comprises the steps of:
(i) providing the following components:
  (a) silk fibroin (a),
  (b) at least one polysaccharide (b) of a molecular weight of at least 100 kDa comprising aldehyde groups in a (molar) ratio between hydroxy groups and aldehyde groups of 100:1 to 2:1, in particular of 90:1 to 5:1,
  (c) at least one liquid carrier (c), in particular water, and
  (d) optionally one or more further components (d);

(ii) mixing (a), (b) and (c), and optionally (d), with another, wherein the total concentration of (a) and (b) in the composition is in the range of from 1 to 50 mg/ml;
(iii) freezing the composition obtained from step (ii);
(iv) lyophilizing the frozen composition obtained from step (iii); and
(v) heating the lyophilized material obtained from step (iv) at a temperature in the range of from 35 to 80° C. for 1 to 10 h.

In a particularly preferred embodiment, the method for preparing a porous material comprises the steps of:
(i) providing the following components:
 (a) silk fibroin (a),
 (b) hyaluronic acid (b) of a molecular weight of at least 100 kDa comprising aldehyde groups in a (molar) ratio between hydroxy groups and aldehyde groups of 100:1 to 2:1, in particular of 90:1 to 5:1,
 (c) at least one liquid carrier (c), in particular water, and
 (d) optionally one or more further components (d);
(ii) mixing (a), (b) and (c), and optionally (d), with another, wherein the total concentration of (a) and (b) in the composition is in the range of from 10 to 40 mg/ml;
(iii) freezing the composition obtained from step (ii);
(iv) lyophilizing the frozen composition obtained from step (iii); and
(v) heating the lyophilized material obtained from step (iv) at a temperature in the range of from 35 to 80° C. for 1 to 10 h.

The porous material obtained from this method may be optionally dried further. The porous material may be stored at any conditions suitable for this purpose such as, e.g., at a temperature in the range of from 2° C. to 6° C., e.g. at approximately 4° C., for example, in a fridge.

As laid out above, depending on the intended use of the porous material of the present invention, it can be beneficial to have a particulate porous material because, for example, a particulate porous material has the advantage that it can be administered to an individual via injection (e.g., via a syringe or a drip).

Therefore, the method of the present invention may comprise one or more further steps for preparing a particulate form of the porous material. In a preferred embodiment, the method comprises a further step (vi) of grinding or milling the porous material obtained from step (v).

Preferably, this step is performed carefully in order to avoid destruction of the porous structure. The temperature should be below temperature ranges disintegrating a fibroin moiety A and a polysaccharide moiety B and a conjugate thereof. The porous material may be cooled during milling. Milling or grinding may be dry milling or grinding or wet milling or grinding. As described above, particle size should be clearly larger than the pore size (i.e. the mean average pore diameter).

The porous material obtainable (or obtained) from the method of the present invention has particularly beneficial properties.

Accordingly, a further aspect of the present invention relates to a porous material obtainable from a method of the present invention. It will be understood that the definitions and preferred embodiments as laid out in the context of the porous material and the methods above mutatis mutandis apply to the porous material obtainable from a method of the present invention.

A further aspect of the present invention relates to an injectable composition comprising a particulate porous material according to the present invention and a liquid or viscous carrier and optionally further components. It will be understood that the definitions and preferred embodiments as laid out in the context of the porous material and the methods above mutatis mutandis apply to the injectable composition of the present invention.

The porous material of the present invention as well as the injectable composition of the present invention may be used for any purpose. Optionally, the porous material may be used for cosmetic and/or therapeutic uses. The injectable composition may be a filler, in particular a soft tissue filler such as, e.g., a dermal filler or a connective tissue filler.

As used herein, the term "filler" may be understood in the broadest sense as any agent that can be used to fill a cavity or to serve as a soft tissue filler, preferably a soft tissue filler. A soft tissue filler may be understood in the broadest sense as a material designed to add volume to areas of soft tissue deficiency. A filler may be administered to any location and by any type of injection and may be suitable for uses in cosmetic/anesthetic applications as well as for therapeutic purposes. A filler may generally be any composition that adds, replaces or augments volume under the skin leading to, e.g., smoothened skin wrinkles, augmented lips, improved skin appearance, or treated scars. It is generally used in the dermis area, such as below the epidermis or above the hypodermis and as such may be injected subcutaneously, hypodermically or intradermally, or some combinations.

An injectable composition within the meaning of the present invention may be administered by means of (dispensed from) syringes under normal conditions under normal pressure. Moreover, the filler composition of the present invention is preferably (essentially) sterile. Preferably, the injectable composition is suitable for injection into a mammal, in particular a human.

Therefor the present invention also relates to the use of an injectable composition comprising a particulate porous material according to the present invention and a liquid or viscous carrier and optionally further components for injection into a mammal, in particular a human, in need thereof.

A liquid or viscous carrier according the present invention may be any injectable carrier. Typically, the liquid or viscous carrier will be a pharmaceutically acceptable carrier, therefore, a carrier that is non-toxic to the mammal in particular a human.

The liquid or viscous carrier may preferably comprise or consist of one or more solvents such as, e.g., water, an aqueous buffer (e.g., a saline or phosphate buffered saline), dimethyl sulfoxide (DMSO), ethanol, vegetable oil, paraffin oil or combinations thereof. More preferably, the liquid or viscous carrier comprises or consists of an apyrogenic isotonic buffer, more particularly a physiological saline solution or a buffered physiological saline solution.

An optionally present further components may be any components. For example, such further component may be selected from the group consisting of one or more local anesthetics, one or more cell proliferation factors, one or more dyes, and combinations of two or more thereof.

A local anesthetic may make injection into an individual more comfortable. A cell proliferation factor may improve cellular invasion into an administered porous material. A dye may either improve localization of the injection (e.g., a pharmaceutically acceptable fluorescent dye like fluorescein or rhodamine) or may improve invisibility of the otherwise whitish porous material (e.g., by rendering it flesh-colored). Any other pharmaceutically active compound may also be added. Then, the porous material of the present invention may also serve as a retard form for administration.

As indicated above, the porous material of the present invention as well as the injectable composition of the present invention may be used for any purpose. Optionally, the porous material may be used for cosmetic and/or therapeutic uses.

Accordingly, the present invention also refers to the use of an injectable composition according to the present invention as a filler such as a dermal filler or a connective tissue filler.

The present invention also refers to the use of an injectable composition according to the present invention for cosmetic applications. More preferably, the present invention also refers to the use of an injectable composition according to the present invention for cosmetic applications comprising facial and body re-shaping and rejuvenation.

Accordingly, a still further aspect of the present invention refers to the use of an injectable composition according to the present invention for cosmetic applications comprising facial and body re-shaping and rejuvenation, including filling of wrinkles, improving facial lines, breast reconstruction or augmentation, rejuvenation of the skin, buttocks augmentation, remodeling of cheekbones, soft-tissue augmentation, filling facial wrinkles, improving glabellar lines, improving nasolabial folds, improving marionette lines, improving buccal commissures, improving peri-lip wrinkles, improving crow's feet, improving subdermal support of the brows, malar and buccal fat pads, improving tear troughs, nose, augmentation of lips, augmentation of cheeks, augmentation of peroral region, augmentation of infraorbital region, resolving facial asymmetries, improving jawlines, and augmentation of chin.

This use may be a therapeutic and/or cosmetic use. Thus, in other words, the present invention relates to an injectable composition according to the present invention for use in a method for facial and body re-shaping and rejuvenation. More preferably, the present invention relates to an injectable composition according to the present invention for use in a method for facial and body re-shaping and rejuvenation, including filling of wrinkles, improving facial lines, breast reconstruction or augmentation, rejuvenation of the skin, buttocks augmentation, remodeling of cheekbones, soft-tissue augmentation, filling facial wrinkles, improving glabellar lines, improving nasolabial folds, improving marionette lines, improving buccal commissures, improving peri-lip wrinkles, improving crow's feet, improving subdermal support of the brows, malar and buccal fat pads, improving tear troughs, nose, augmentation of lips, augmentation of cheeks, augmentation of peroral region, augmentation of infraorbital region, resolving facial asymmetries, improving jawlines, and augmentation of chin.

The present invention also relates to a method of facial and body re-shaping and rejuvenation (preferably including the above specific uses), said method comprising administering the injectable composition according to the present invention.

It will be understood that the definitions and preferred embodiments as laid out in the context of the porous material, the methods and the injectable composition above mutatis mutandis apply to the use of the injectable composition of the present invention.

Re-shaping may be performed for cosmetic purposes or may be performed after loss of tissue such as, e.g., caused by an accident or by a surgical intervention. For instance, a part of the face may be injured by an accident. On the other hand, cheekbones may be accentuated by filling the cheekbone region subcutaneously. A breast or part thereof may be surgically removed. On the other hand, breast reconstruction or augmentation may also have aesthetic reasons.

Preferably, the injectable composition of the present invention may be administered in an effective amount to an individual by injection, such as by subcutaneous or intradermal injection. In a preferred embodiment, in the context of this use, the injectable composition is a filler. In a more preferred embodiment, in the context of this use, the injectable composition is a filler and the use comprises the administration of the composition comprising particulate porous material in the tissue of interest, in particular subcutaneously or intradermally. For example, the injectable composition may be intradermally or subcutaneously injected using the serial puncture technique. An effective amount refers to the amount of the (injectable) soft tissue filler composition sufficient to effect beneficial or desired cosmetic (aesthetic) or therapeutic results.

In a particularly preferred embodiment, in the context of this use, the injectable composition is a filler, in particular a soft tissue filler, and the use comprises administration of the composition comprising particulate porous material subcutaneously or intradermally. For these uses, the porous material according to the present invention is particularly beneficial because the porous material rather stable in aqueous environments such as body fluids and enables invasion of cells due to its porous structure and surface characteristics.

A further aspect of the present invention relates to the porous material or the injectable composition according to the present invention for use in a method for regenerating tissue of an individual in need thereof.

In other words, the present invention also relates to a method for regenerating tissue of an individual in need thereof, said method comprising administration of the porous material or the injectable composition according to the present invention to the individual in need thereof. Regenerating tissue of an individual in need thereof may be performed for therapeutic and/or cosmetic purposes.

It will be understood that the definitions and preferred embodiments as laid out in the context of the porous material, the methods and the injectable composition above mutatis mutandis apply to the use of regenerating tissue of an individual.

The tissue to be regenerated may be any tissue. In one preferred embodiment, the tissue is a soft tissue. In a more preferred embodiment, the tissue is a soft tissue selected from the group consisting of dermal tissue (including tissue of the dermis and the subcutis) and connective tissue. Then, the method may be used for re-shaping and rejuvenation, including the uses as described above. In another preferred embodiment of the present invention, the tissue is an articulation (joint) tissue. Optionally, for this use, the porous material may comprise one or more cell proliferation factors stimulating proliferation of the respective tissue.

In an alternative preferred embodiment, the tissue is bone tissue. Then, the porous material of the present invention may be administered in a location where bone tissue is intended to grow such as e.g., in a gap of a bone fracture or for elongation of bones. Optionally, for this use, the porous material may comprise one or more cell proliferation factors stimulating bone cell proliferation.

Depending on the specific use, the person skilled in the art will either use particulate porous material according to the present invention or will use a block of the porous material according to the present invention.

For the above therapeutic and cosmetic uses, the porous material according to the present invention is particularly beneficial because the porous material is rather stable in aqueous environments such as body fluids and enables invasion of cells due to its porous structure and surface characteristics.

As indicated above, the porous material of the present invention is obtained by the inventive material obtained when conjugating one or more fibroin moieties A with one or more polysaccharide moieties B. This conjugate as such also bears unexpectedly beneficial properties.

Accordingly, a still further aspect of the present invention refers to a fibroin conjugate comprising:
one or more fibroin moieties A; and
one or more polysaccharide moieties B,
wherein the fibroin moieties A and the polysaccharide moieties B are directly conjugated with another without an interconnecting linker structure.

It will be understood that the definitions and preferred embodiments as laid out in the context of the porous material and the methods above mutatis mutandis apply to the conjugate of the present invention.

As used herein, the terms "approximately" and "about" may be understood as a scope including a deviation of up +/−10% of the respective number value. It will be understood that the specific values are also explicitly disclosed.

It will be further understood that the scope embraces the number values provided as commonly rounded values that embrace the whole rounding limits. For example, the scope of "1 mg" embraces the range of from 0.50 to 1.49 mg.

The number values of the present invention, however, also disclose the more detailed values of one or more orders of magnitude more in detail. Accordingly, for example, "1 mg" may also include the specific disclosure of "1.0 mg".

The Figures and Examples and claims described below are intended to illustrate, without any limitation, further embodiments of the present invention.

ABBREVIATIONS

Figure 1:
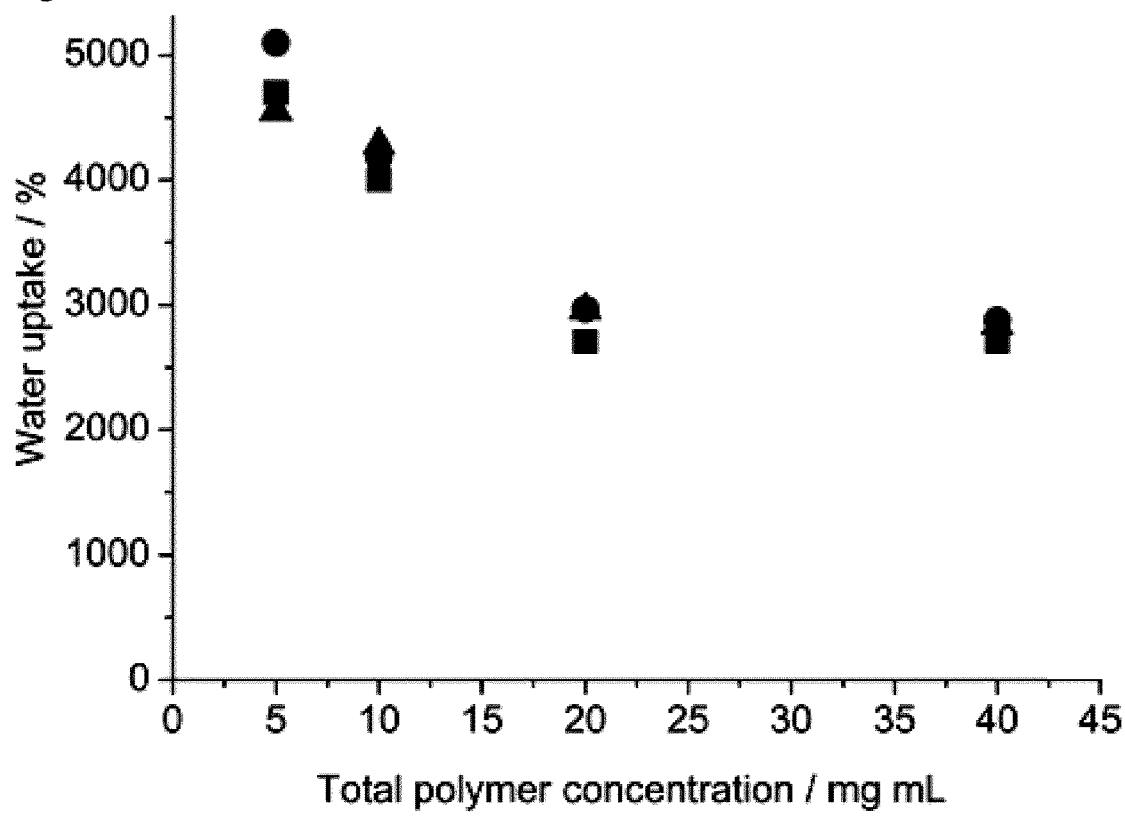
FIG. 1 shows the influence of the total polymer concentration used in the process according to the present invention (fibroin:formyl HA (MoD: 7%, Mw: 841 kDa) mass ratio of 1:1, annealing: 3 h at 50° C.) on water uptake after different incubation times at room temperature (RT) (squared: 2 h, circular: 17 h, triangular: 24 h).

Formyl HA: aldehyde modified hyaluronic acid;
HA: hyaluronic acid;
MoD: modification degree (molar ratio of hydroxy groups oxidized into aldehyde groups)
mol %: mole percent
Mw: (weight average) molecular weight
RT: room temperature, i.e., approximately 20° C.
wt. % percent by weight
Further abbreviations used herein are those of the International Union of Pure and Applied Chemistry (IUPAC) nomenclature as far as not otherwise defined herein. The following examples and claims further illustrate the invention.

EXAMPLES

Example 1—Preparation of the Porous Material

I) Materials
The following equipment was used:
Purified water system (ELIX 20)
Freeze drier (lyophilization equipment) (Christ, Alpha 1-2 LDplus)
Oven (MMM group, Venticell)

TABLE 1

| Materials | | |
|---|---|---|
| Material | Batch Number | Supplier |
| Formyl HA (aldehyde modified hyaluronic acid) | EL28 (Mw = 67 kDa, MoD = 4%) HAox180116 (Mw = 66 kDa, MoD = 9%) EL30 (Mw = 314 kDa, MoD = 4%) VH188 (Mw = 804 kDa, MoD = 4%) 270116 (Mw = 841 kDa, MoD = 7%) | Contipro |
| Fibroin | 5154-20ML (7505) | Advanced BioMatrix, USA |

TABLE 1-continued

| Material | Batch Number | Supplier |
|---|---|---|
| Fibroin | CSK10-1051 (FA1S0417) | CareSilk, Italy |
| Purified Water | — | internal |

II) Methods

In summary, the preparation was performed by the following consecutive steps:
  (i) Proving: (a) a fibroin solution and (b) a formyl HA solution;
  (ii) Mixing (a) and (b);
  (iii) Freezing the composition;
  (iv) Lyophilization; and
  (v) Water vapor annealing.

In this method, it was found that in steps (iii) and (iv) pores are formed (pore formation). Further, it was found that step (v) stabilizes the pores via chemical crosslinking and crystallization of fibroin. These steps are performed as follows:

Step (i)—Providing of the Solutions
(a) Preparation of Formyl HA Solution:

Formyl HA powder was weighted, followed by addition of required amount of purified water in order to obtain desired polymer concentration (in the range of from 5 to 40 mg/ml) and the mixture was left in a fridge during the night to insure complete dissolution of the polymer.

(b) Preparation of Fibroin Solution:

Fibroin purchased from both producers (Advanced BioMatrix, USA and CareSilk, Italy) was delivered as a water solution with the concentration of 50 mg/ml and was always stored in a deep-freezer at the temperature of −80° C. Therefore, to be able to use it, solution was taken a day before from the deep-freezer and placed in a fridge (at +4° C.) to insure slow melting of the solution. When the fibroin solution was melted, it was carefully diluted with purified water to obtain desired concentration (in the range of from 5 to 40 mg/ml).

Step (ii)—Mixing

Two solutions were mixed carefully to obtain one homogeneous solution, which was thereafter poured in a Teflon dish.

Step (iii)—Freezing

Teflon dish containing mixture of Formyl HA and Fibroin was placed in a freezer at −20° C. overnight.

Step (iv)—Lyophilization

Thereafter, frozen solution was placed in a freeze-dryer and was left inside for a few days until all water was removed.

Step (v)—Water Vapor Annealing

Dry sample, after being taken from the Teflon dish was treated with the water vapor in an oven at different temperatures (from 30° C. till 70° C.) for different time (from 0.5 till 6 h). It was taken care that the samples did not come in contact with liquid water but were treated only with warm water vapor. When the treatment was over, sample was placed in a vial and stored in a fridge at 4° C.

Example 1—Testing Stability in Aqueous Solutions

Porous materials were prepared according to steps (i) to (iv) of the above description as far as not indicated otherwise. Blocks of a diameter of approximately 1-2 cm were prepared. These blocks were either directly contacted with water (indicated by "−" in the below Table) or subjected to water vapor annealing according to step (v) of the above description (indicated by "+" in the below Table). All samples were then and contacted with water and stored for one day in water at room temperature (RT).

TABLE 2

Comparison between porous materials obtained by different preparations

| No. | Fibroin [wt. %] | HA [wt. %] | Formyl HA [wt. %] | Water Vapor annealing | Appearance after storage in water for one day at RT |
|---|---|---|---|---|---|
| I | 0 | 100 | 0 | − | disintegrated, essentially clear |
| II | 0 | 100 | 0 | + | disintegrated, essentially clear |
| III | 25 | 75 | 0 | − | disintegrated, whitish and turbid |
| IV | 25 | 75 | 0 | + | disintegrated, whitish and turbid |
| V | 75 | 25 | 0 | − | disintegrated, whitish and turbid |
| VI | 75 | 25 | 0 | + | disintegrated, whitish and turbid |
| VII | 0 | 0 | 100 | − | disintegrated, essentially clear |
| VIII | 0 | 0 | 100 | + | partly disintegrated |
| IX | 25 | 0 | 75 | − | extensively disintegrated, clear |
| X | 25 | 0 | 75 | + | intact, clearly shaped block | herein: material X is according to the present invention; materials I-IX are for comparative purposes; and the weight percentages refer to the total mass of the high-molecular weight components (i.e., A: fibroin and B: hyaluronic acid (HA) or aldehyde modified hyaluronic acid (formyl HA)).

In summary, it was surprisingly found that a combination of fibroin and formyl HA subjected to the preparation steps (i)-(v) as described above, including the water vapor annealing step (v), leads to a stable material. When either fibroin was missing in the composition or the water vapor annealing step (v) was missing, a significant less stable material was obtained. When formyl HA was replaced by unmodified HA (i.e., not oxidized HA), the material completely disintegrated.

A further observation was that materials II, IV, and VI, i.e., the materials comprising HA instead of Formyl HA, showed significant shrinkage when subjected to the step (v) of water vapor annealing. Materials VII and X, i.e., the materials comprising Formyl HA showed far less shrinkage when subjected to the step (v) of water vapor annealing. The porous materials X according to the present invention was particularly stable and showed a low degree of shrinkage.

Example 2—Comparison Between Different Preparations

Porous materials were prepared according to steps (i) to (v) of the above description. The influence of different parameters on water uptake was determined. Water uptake is also an indicator for swelling.

a) Influence of the Total Polymer Concentration on Water Uptake

Fibroin (Advanced BioMatrix) was reacted with formyl HA (modification degree (MoD): 7%, Mw: 841 kDa) In the process, a fibroin solution containing 20 mg/ml fibroin and a formyl HA solution containing 20 mg/ml were used at a formyl HA: fibroin ratio of 1:1. In the preparation as described above, different total polymer concentrations of 5 mg/ml, 10 mg/ml, 20 mg/ml and 40 mg/ml were used. The annealing step (v) was performed at 50° C. for 3 h. The obtained porous materials were contacted with water and swelling was observed over time at room temperature (RT). The water content for all samples was determined after 2 h, 17 h and 24 h.

The results are depicted in FIG. 1. It was found that in all samples resulted in stable porous materials that and swelling did not increase significantly over time. This indicates that all porous materials were highly stable in water for more than 24 h. When using a total polymer concentration of 5 mg/ml, the obtained porous material absorbed nearly the 50fold mass of water, related to the dry weight of the porous material. When using a total polymer concentration of 10 mg/ml, the obtained porous material absorbed approximately the 40fold mass of water, related to the dry weight of the porous material. When using a total polymer concentration of 20 or 40 mg/ml, the obtained porous material absorbed slightly less than the 30 fold mass of water, related to the dry weight of the porous material. Interestingly, there was essentially no difference in water uptake capacity between the two latter porous materials. This comparison shows that a wide range of polymer concentration can be used in the context of the present invention. The ranges of at least 10 mg/ml, in particular at least 20 mg/ml, lead to particularly stable porous materials. When stability is desired the person skilled in the art may use higher polymer concentrations. When higher water absorbance is desired, the person skilled in the art may use lower polymer concentrations.

b) Influence of Formyl HA: Fibroin Ratio

Fibroin (Advanced BioMatrix) was reacted with formyl HA (MoD: 7%, Mw: 841 kDa). In the process, a fibroin solution containing 20 mg/ml fibroin and a formyl HA solution containing 20 mg/ml were used at different formyl HA: fibroin ratios of 1:0, 3:1, 1:1, 1:3 and 0:1. The annealing step (v) was performed at 50° C. for 3 h. The obtained porous materials were contacted with water and swelling was observed over time at room temperature (RT). The water content for all samples was determined after 2 h, 17 h and 24 h.

Figure 2:
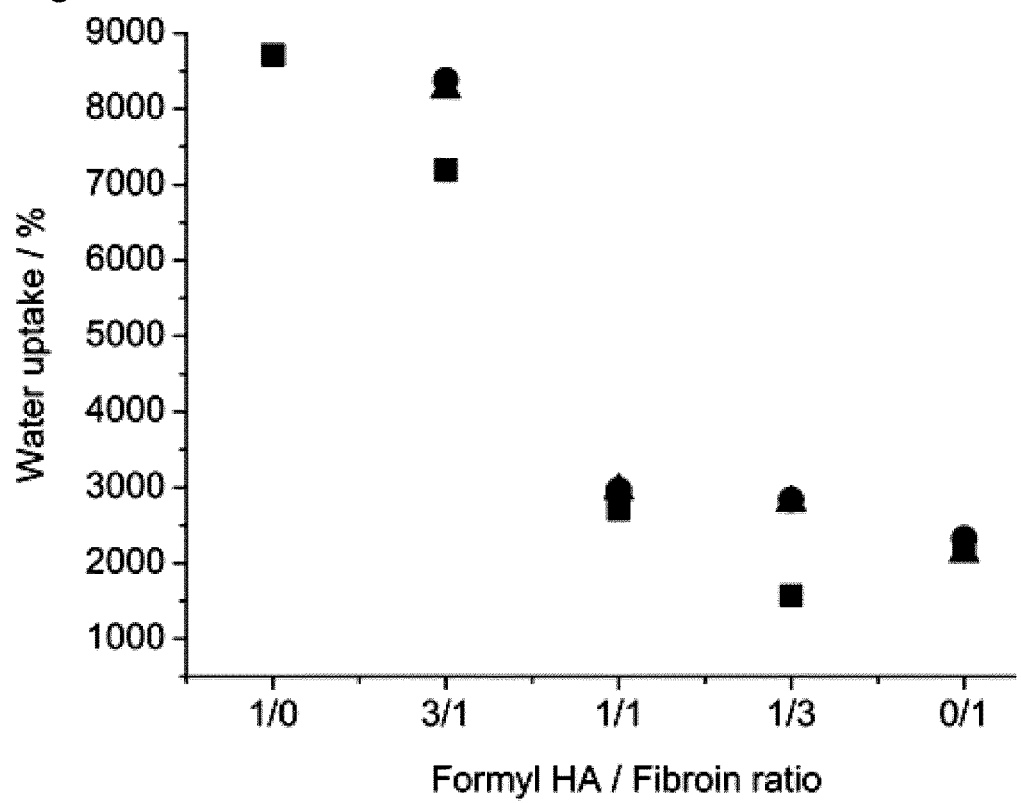
FIG. 2 shows the influence of formyl HA: fibroin mass ratio used in the process according to the present invention (formyl HA (MoD: 7%, Mw: 841 kDa), annealing: 3 h at 50° C.) on water uptake after different incubation times at room temperature (RT) (squared: 2 h, circular: 17 h, triangular: 24 h).

The results are depicted in FIG. 2. It was found that a material free of fibroin (i.e., obtained from a formyl HA: fibroin ratio of 1:0) disintegrated overtime. After 2 h, the material already absorbed nearly the 90fold mass of water, related to the dry weight of the porous structure. After 17 h, the material was essentially disintegrated. A formyl HA: fibroin ratio of 3:1 resulted in a porous material that swelled to a large extend to up a degree absorbing more than the 80 fold mass of water, related to the dry weight of the porous structure. Formyl HA: fibroin ratios of 1:1 and 1:3 resulted in highly stable porous materials that absorbed approximately the 30 fold mass of water, related to the dry weight of the porous structure. The stability of these structures was comparable to a porous material composed of fibroin only (i.e., obtained from a formyl HA: fibroin ratio of 0:1). This comparison shows that a wide range of formyl HA: fibroin ratio can be used in the context of the present invention. The ranges of formyl HA: fibroin ratios wherein considerably contents of both polymers are present lead to particularly stable porous materials that still bear the beneficial properties of both polymers.

c) Influence of the Molecular Weight of Formyl HA

Fibroin (Advanced BioMatrix) was reacted with formyl HA (MoD: 4%). In the process, a fibroin solution containing 20 mg/ml fibroin and a formyl HA solution containing 20 mg/ml were used at a formyl HA: fibroin ratio of 1:1. Formyl HA polymers of different molecular weight (Mw) of less than 10 kDa, approximately 300 kDa, and approximately 800 kDa were used. The annealing step (v) was performed at 50° C. for 3 h. The obtained porous materials were contacted with water and swelling was observed over time at room temperature (RT). The water content for all samples was determined after 2 h, 17 h and 24 h.

Figure 3:
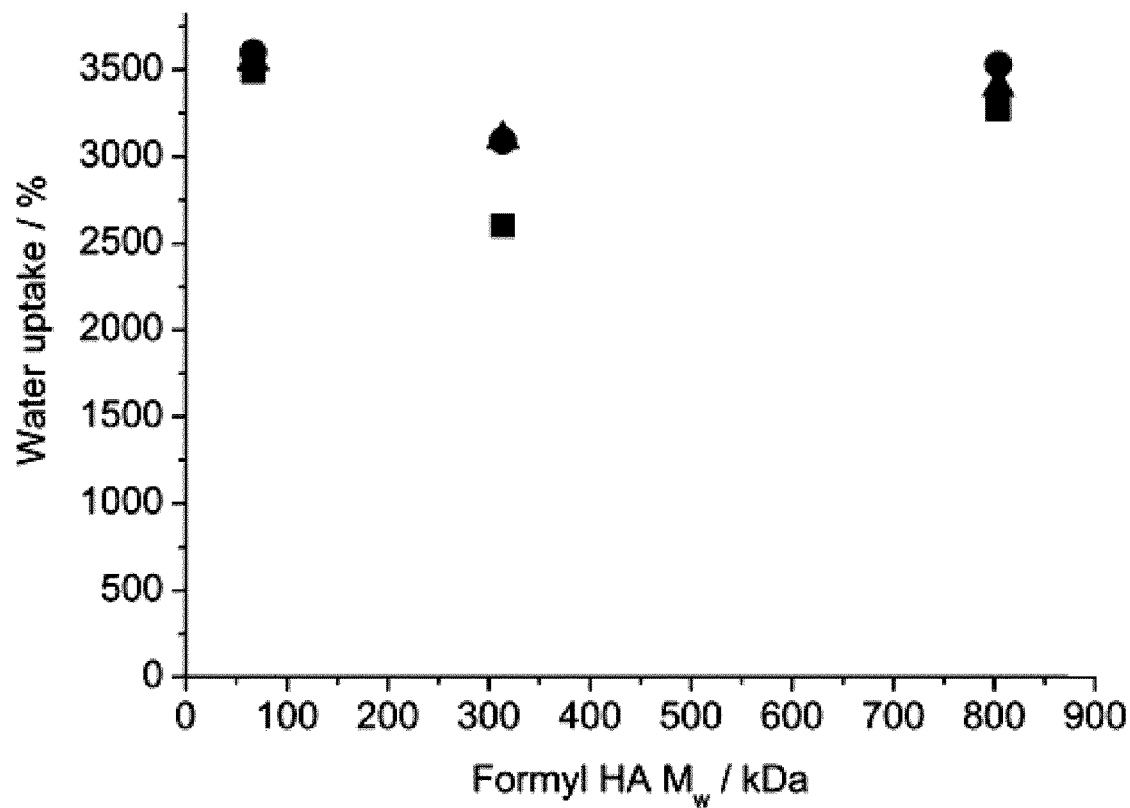
FIG. 3 shows the influence of the molecular weight (Mw) of formyl HA used in the process according to the present invention (fibroin:formyl HA (MoD: 4) mass ratio of 1:1, annealing: 3 h at 50° C.) on water uptake after different incubation times at room temperature (RT) (squared: 2 h, circular: 17 h, triangular: 24 h).

The results are depicted in FIG. 3. It was found that for all samples stable structures were obtained that showed comparable swelling. This comparison shows that a wide range of molecular weight of formyl HA can be used in the context of the present invention.

d) Influence of the Modification Degree of Formyl HA

Figure 4:
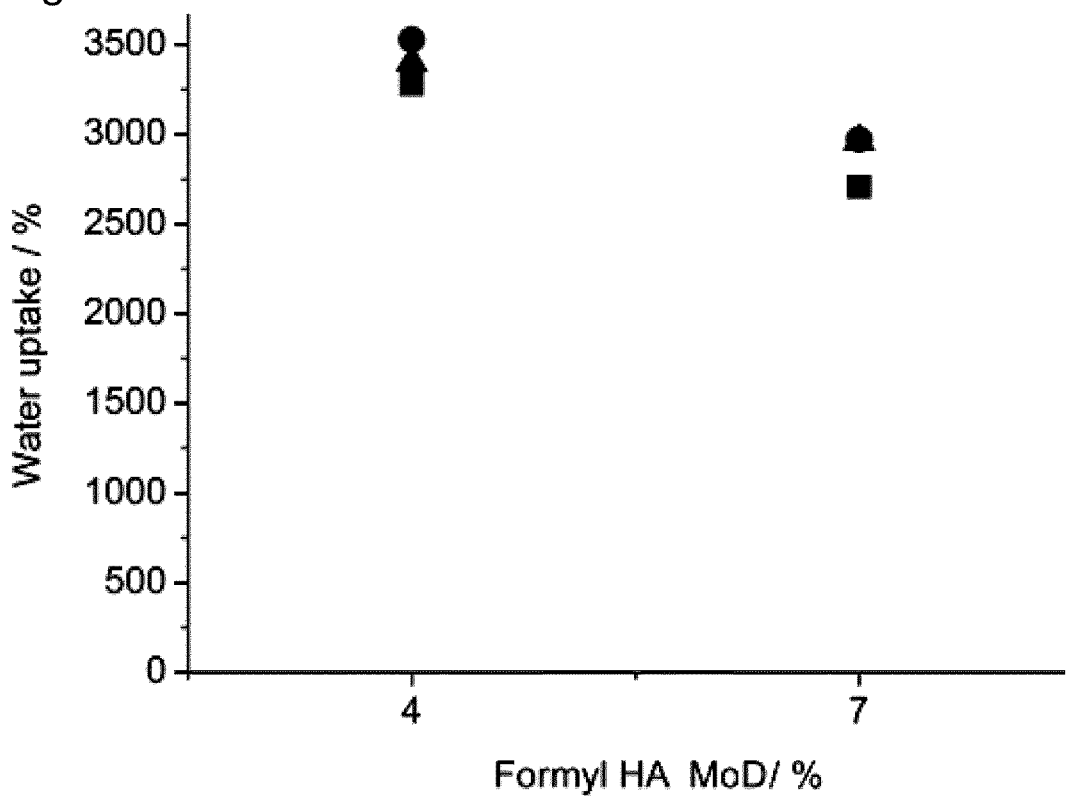
FIG. 4 shows the influence of the modification degree of formyl HA used in the process according to the present invention (fibroin: formyl HA (Mw: approximately 800 kDa) mass ratio of 1:1, annealing: 3 h at 50° C.) on water uptake after different incubation times at room temperature (RT) (squared: 2 h, circular: 17 h, triangular: 24 h).

Fibroin (Advanced BioMatrix) was reacted with formyl HA (Mw: approximately 800 kDa). In the process, a fibroin solution containing 20 mg/ml fibroin and a formyl HA solution containing 20 mg/ml were used at a formyl HA: fibroin mass ratio of 1:1. Formyl HAs with modification degrees (MoDs) of 4 mol % and 7 mol % were used. The annealing step (v) was performed at 50° C. for 3 h. The obtained porous materials were contacted with water and swelling was observed over time at room temperature (RT). The water content for all samples was determined after 2 h, 17 h and 24 h. The results are depicted in FIG. 4. It was found that a modification degree of 7% led to slightly less water absorbance and, thus, swelling. It is assumed that this is due to the somewhat higher degree of crosslinking. This comparison shows that a wide range of modification degree of formyl HA can be used in the context of the present invention. The degree of crosslinking can be adjusted by the modification degree.

e) Influence of the Annealing Temperature

Figure 5:
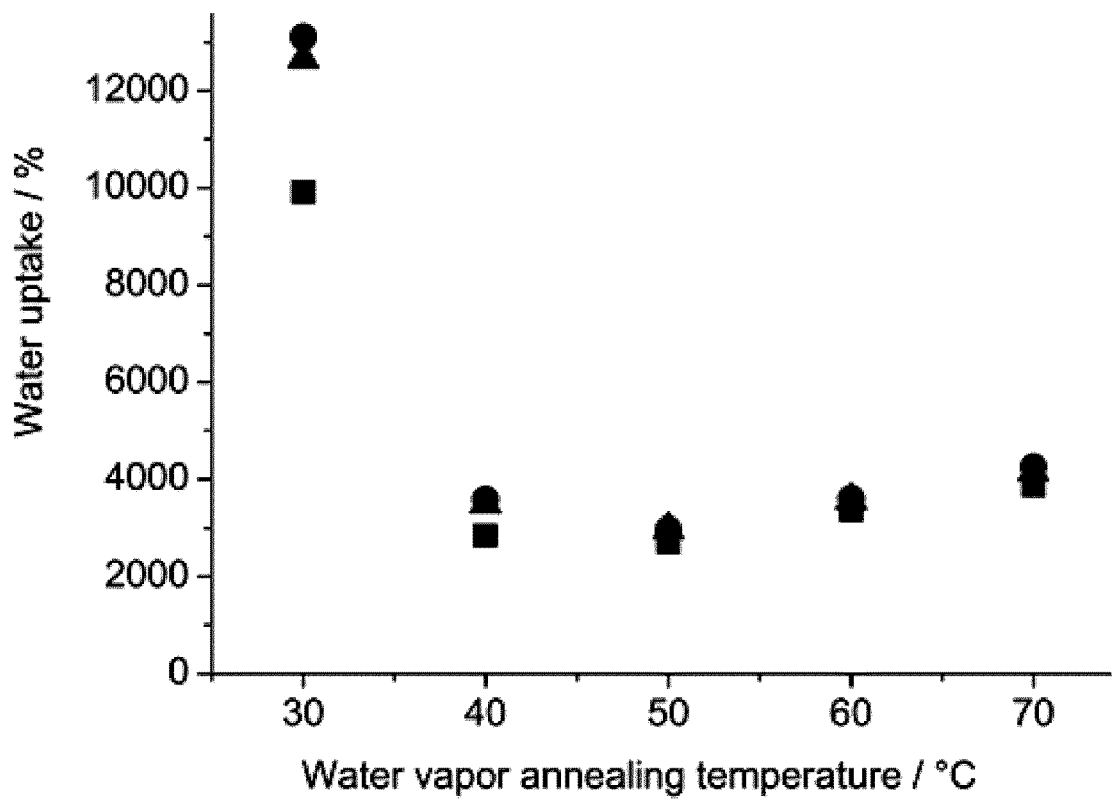
FIG. 5 shows the influence of the annealing temperature used in the process according to the present invention (fibroin: formyl HA (MoD: 7%, Mw: 841 kDa) mass ratio of 1:1, annealing: 3 h) on water uptake after different incubation times at room temperature (RT) (squared: 2 h, circular: 17 h, triangular: 24 h).

Fibroin (Advanced BioMatrix) was reacted with formyl HA (MoD: 7%, Mw: 841 kDa). In the process, a fibroin solution containing 20 mg/ml fibroin and a formyl HA solution containing 20 mg/ml were used at a formyl HA: fibroin mass ratio of 1:1. The annealing step (v) was performed for 3 h at different temperatures of 30° C., 40° C., 50° C., 60° C. and 70° C. The obtained porous materials were contacted with water and swelling was observed over time at room temperature (RT). The water content for all samples was determined after 2 h, 17 h and 24 h. The results are depicted in FIG. 5. It was found that temperatures from 30-40° C. upwards, in particular of at least 40° C., led to a widely constant range of swelling. Interestingly, a maximum of stability (low swelling) was observed at a temperature of 50° C. This comparison shows that a wide range of temperatures from 40 to 70° C. can be used for annealing in the context of the present invention. Temperatures around 50° C. may be particularly beneficial.

f) Influence of the Annealing Time

Figure 6:
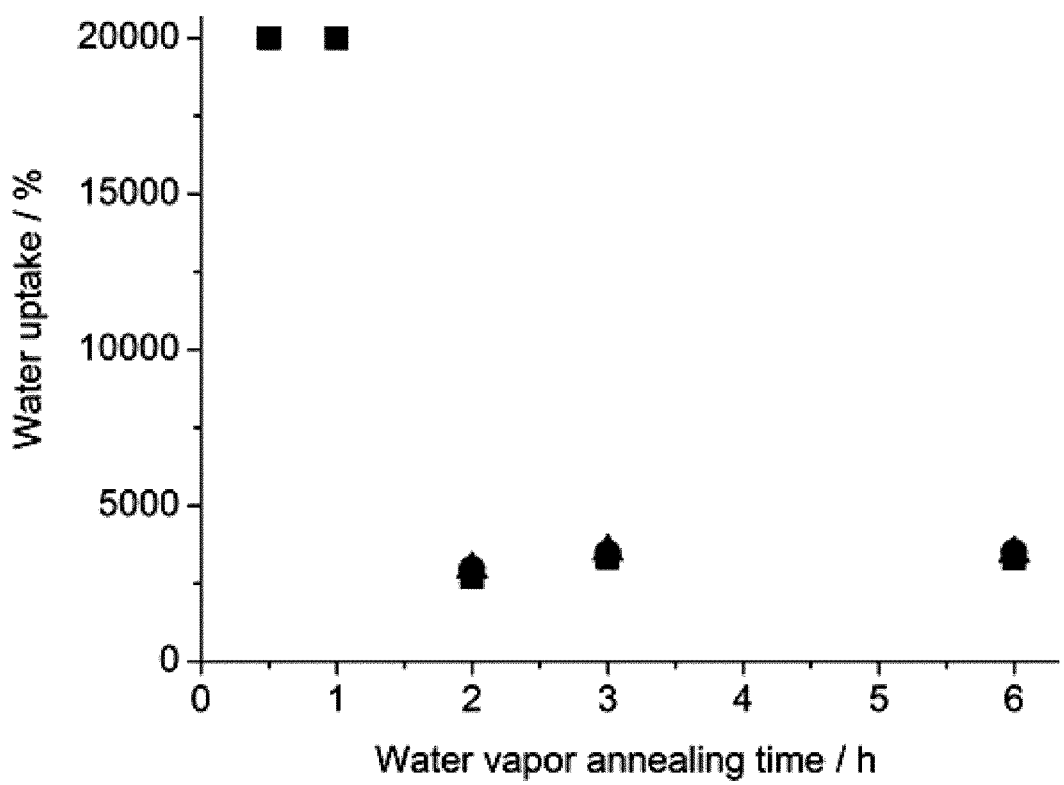
FIG. 6 shows the influence of the annealing time used in the process according to the present invention fibroin: formyl HA (MoD: 7%, Mw: 841 kDa) mass ratio of 1:1, annealing at 50° C.) on water uptake after different incubation times at room temperature (RT) (squared: 2 h, circular: 17 h, triangular: 24 h).

Fibroin (Advanced BioMatrix) was reacted with formyl HA (MoD: 7%, Mw: 841 kDa). In the process, a fibroin solution containing 20 mg/ml fibroin and a formyl HA solution containing 20 mg/ml were used at a formyl HA:fibroin mass ratio of 1:1. The annealing step (v) was performed at 50° C. for different times of 30 min, 1 h, 2 h, 3 h and 6 h. The obtained porous materials were contacted with water and swelling was observed over time at room temperature (RT). The water content for all samples was determined after 2 h, 17 h and 24 h. The results are depicted in FIG. 6. It was found that, at a temperature of 50° C., an annealing time of 30 min and 1 h, respectively, was not sufficient when it is intended to obtain a stable structure. Annealing times from 1-2 h upwards, in particular of at least 2 h, led to an essentially constant range of swelling. Interestingly, a maximum of stability (low swelling) was observed for an annealing time of 3 h. This comparison shows that a wide range of annealing times can be used for annealing in the context of the present invention.

g) Further Findings

Furthermore, it was found that different fibroin batches and different storage conditions of the fibroin and the prepared porous materials led to somewhat different stabilities of the porous materials in aqueous environments. Storage of fibroin in frozen state, in particular at −80° C., was found to be particularly advantageous.

Example 3—Scanning Electron Microscopy (SEM)

Figure 7:
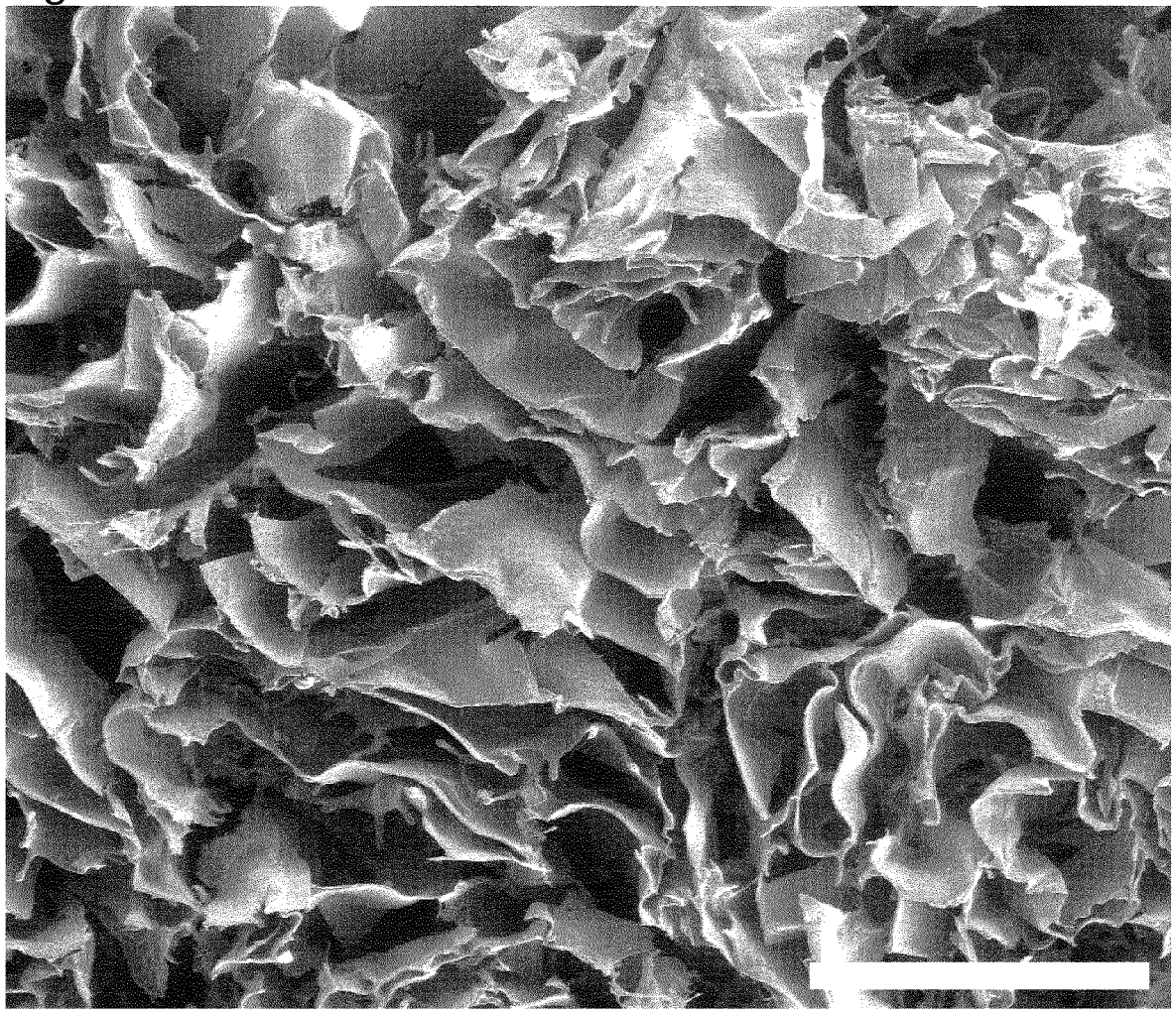
FIG. 7 shows the appearance of the dry porous material (magnification 200 fold, HV: 5.0 kV, WD: 5.3 mm, Det LFD, pressure: 100.0 Pa, HFW 1.35 mm). The white scale bar indicates 400 μm.
Figure 8:
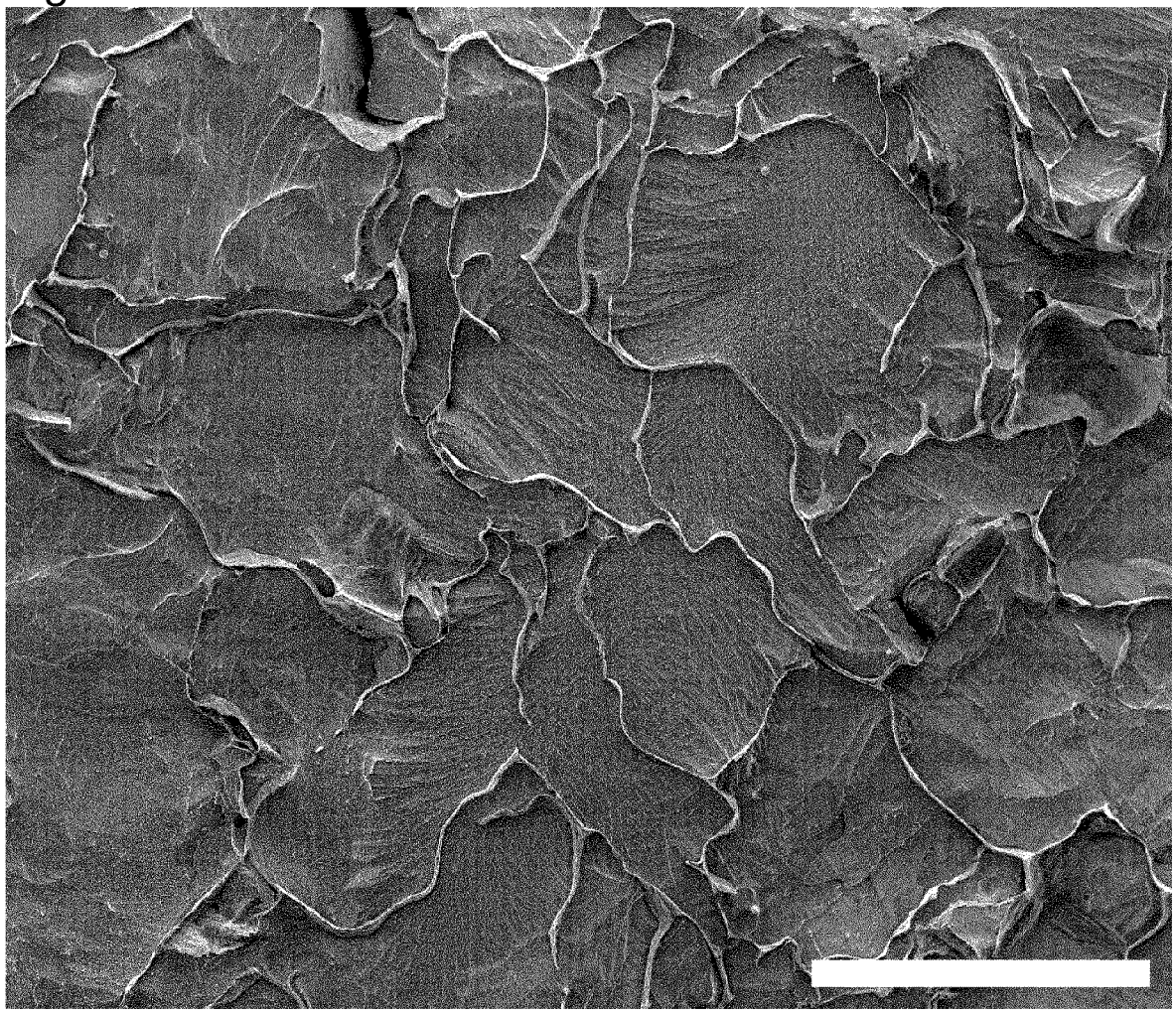
FIG. 8 shows the appearance of the porous material swollen in water (magnification 200 fold, HV: 3.0 kV, WD: 12.0 mm, Det ETD, pressure: -, HFW 1.35 mm). The white scale bar indicates 400 μm.

Porous materials obtained by a process of the present invention were investigated by scanning electron microscopy (SEM). Dry and the water-moist porous materials were compared with another. The porous structure was found in the dry state as well as in the moist state. The mean average pore diameter was in the range of from 20 to 400 μm. Pores appeared more circular in the swelled structure of the water-moist porous material in comparison to the dry counterpart. The appearance of the dry porous material and the porous material swollen in water is depicted in FIGS. 7 and 8.

The invention claimed is:

1. A porous material having a scaffold comprising:
one or more fibroin moieties A; and
one or more hyaluronic acid (HA) moieties B,
wherein A and B are directly covalently conjugated to one another without an interconnecting linker structure via a reaction of one or more aldehyde groups of B with an epsilon amino group of a lysyl residue of A,
wherein said porous material has pores with an overall inner pore volume, wherein the pores are filled with air in a dry state and with a liquid or a viscous fluid in a wet state, and an overall volume of solid content of said porous material, and
wherein, in an uncompressed form, the sum of the overall inner pore volume of the porous material is larger than the overall volume of the solid content of the porous material.

2. The porous material of claim 1, wherein one or more lysyl residues of the one or more fibroin moieties A are directly covalently bound to one or more carbon atoms of the one or more hyaluronic acid (HA) moieties B via double bond or via single bond.

3. The porous material of claim 1, wherein the one or more hyaluronic acid (HA) moieties B have a weight average molecular weight in the range of 50 to 2000 kDa.

4. The porous material of claim 1, wherein the ratio between fibroin moieties A and hyaluronic acid (HA) moieties B is in the range of 1:10 to 10:1.

5. The porous material of claim 1, wherein said porous material bears pores of a mean average pore diameter in the range of from 20 to 400 μm.

6. The porous material of claim 5, wherein said porous material is particulate and bears a mass average particle size that is at least 5-fold larger than the mean average pore diameter.

7. A method for preparing a porous material, comprising the steps of:
(i) providing the following components:
(a) fibroin (a),
(b) at least one polysaccharide (b) comprising aldehyde groups,
(c) at least one liquid carrier (c), and
(d) optionally one or more further components (d);
(ii) mixing (a), (b), (c), and optionally (d) with another to obtain a composition;
(iii) freezing the composition obtained from step (ii);
(iv) lyophilizing the frozen composition obtained from step (iii); and
(v) heating the lyophilized material obtained from step (iv) to 40 to 70° C. suitable for enabling the formation of covalent bonds between (a) and (b) and removal of residual liquid carrier (c).

8. The method of claim 7, wherein the porous material has a scaffold comprising:
one or more fibroin moieties A; and
one or more polysaccharide moieties B,
wherein A and B are directly conjugated to one another without an interconnecting linker structure.

9. The method of claim 7, wherein the at least polysaccharide (b) comprises a ratio between hydroxy groups and aldehyde groups of 100:1 to 2:1.

10. The method of claim 7, wherein in step (ii) the total concentration of polymer components (a) and (b) in the composition is in the range of from 1 to 50 mg/ml.

11. The method of claim 7, wherein in step (v) the lyophilized material is heated at a temperature in the range of from 40 to 60° C. for 2 to 6 hours.

12. The method of claim 7, wherein said method comprises a further step (vi) of grinding or milling the porous material obtained from step (v).

13. A porous material obtainable from a method of claim 7.

14. An injectable composition comprising a particulate porous material of claim 1 and a liquid or viscous carrier and optionally further components.

15. A method of use of an injectable composition of claim 14 for cosmetic applications comprising the step of injecting the injectable composition into an individual mammal via a syringe or a drip for facial and body re-shaping and rejuvenation.

16. The method of claim 15, wherein the facial and body re-shaping and rejuvenation is selected from the group consisting of filling of wrinkles, improving facial lines, breast reconstruction or augmentation, rejuvenation of the skin, buttocks augmentation, remodeling of cheekbones, soft-tissue augmentation, filling facial wrinkles, improving glabellar lines, improving nasolabial folds, improving marionette lines, improving buccal commissures, improving peri-lip wrinkles, improving crow's feet, improving subdermal support of the brows, malar and buccal fat pads, improving tear troughs, nose, augmentation of lips, augmentation of cheeks, augmentation of peroral region, augmentation of infraorbital region, resolving facial asymmetries, improving jawlines, and augmentation of chin.

17. A method for regenerating tissue of an individual comprising the step of administering the porous material of claim 1 to an individual in need thereof.

18. A method for regenerating tissue of an individual comprising the step of administering the injectable composition of claim 14 to an individual in need thereof.

19. A fibroin conjugate comprising:
   one or more fibroin moieties A; and
   one or more hyaluronic acid (HA) moieties B,
   wherein the fibroin moieties A and the hyaluronic acid (HA) moieties B are directly covalently conjugated to one another without an interconnecting linker structure via a reaction of one or more aldehyde groups of B with an epsilon amino group of a lysyl residue of A,
   wherein the molar ratio of hydroxyl groups to aldehyde groups in the one or more hyaluronic acid (HA) moieties B at the onset of reaction was in the range of 100:1 to 2:1.

* * * * *